US00PP21616P2

(12) United States Plant Patent
Pan

(10) Patent No.: US PP21,616 P2
(45) Date of Patent: Jan. 11, 2011

(54) ***LANTANA* PLANT NAMED 'BANI ROSSA'**

(50) Latin Name: *Lantana camara L.*
Varietal Denomination: Bani Rossa

(75) Inventor: Shifeng Pan, Hollister, CA (US)

(73) Assignee: Synegenta Crop Protection AG, Basel (CH)

( * ) Notice: Subject to any disclaimer, the term of this patent is extended or adjusted under 35 U.S.C. 154(b) by 0 days.

(21) Appl. No.: 12/589,238

(22) Filed: Oct. 20, 2009

(51) Int. Cl.
*A01H 5/00* (2006.01)

(52) U.S. Cl. ..... Plt./227

(58) Field of Classification Search ..... Plt./227
See application file for complete search history.

*Primary Examiner*—June Hwu
*Assistant Examiner*—Louanne C Krawczewicz Myers
(74) *Attorney, Agent, or Firm*—S. Matthew Edwards

(57) ABSTRACT

A new *Lantana* plant named 'Bani Rossa,' particularly distinguished by the large sized, bold yellow flowers that turn red-purple, excellent floriferousness, a result of limited seed set, compact and dense mounding habit with dark green foliage.

1 Drawing Sheet

Latin name of the genus and species of the plant claimed: *Lantana camara L.*

Varietal denomination: 'Bani Rossa'.

BACKGROUND OF THE NEW PLANT

The present invention comprises a new *Lantana,* botanically known as *Lantana camara L.* and hereinafter referred to by the variety name 'Bani Rossa.'

'Bani Rossa' is a product of a planned breeding program. The new cultivar 'Bani Rossa' has large sized, bold yellow flowers that turn red-purple, excellent floriferousness, a result of limited seed set, compact and dense mounding habit with dark green foliage.

'Bani Rossa' originates from a self pollination in a controlled breeding program in Gilroy, Calif. The pollination was made in June 2004 and the seed sown in February 2005. The female parent was an unpatented, proprietary plant identified as '93-2' with rose color. '93-2' has lighter red flowers, larger and lighter foliage and a more open and taller plant habit than 'Bani Rossa.'

'Bani Rossa' was selected as one flowering plant within the progeny of the stated cross in June 2005 in a controlled environment in Gilroy, Calif.

The first act of asexual reproduction of 'Bani Rossa' was accomplished when vegetative cuttings were propagated from the initial selection in the June 2005 in a controlled environment in Gilroy, Calif.

BRIEF SUMMARY OF INVENTION

Horticultural examination of plants grown from cuttings of the plant initiated in June 2005 in Gilroy, Calif., and continuing thereafter, has demonstrated that the combination of characteristics as herein disclosed for 'Buni Rossa' are firmly fixed and are retained through successive generations of asexual reproduction.

'Bani Rossa' has not been observed under all possible environmental conditions. The phenotype may vary significantly with variations in environment such as temperature, light intensity and day length.

A Plant Breeder's Right for this cultivar was applied for in Canada on Jan. 30, 2009. 'Bani Rossa' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'Bani Rossa' with colors being as true as possible with an illustration of this type. The photographic drawing shows a flowering potted plant of the new variety growing in a 4.5 inch container, and a close up of the flowers.

DETAILED BOTANICAL DESCRIPTION

The plant descriptions, measurements and aforementioned photographs were taken in Gilroy, Calif. in April 2009 in a greenhouse. These plants were growing in 4.5 inch pots in a trial setting. The plants were about 16-18 weeks of age and were grown with several early sprays of Paclobutrazol, a plant growth regular.

Color Chart used: Royal Horticultural Society Colour Chart (R.H.S.) 2001.

TABLE 1

DIFFERENCES BETWEEN THE NEW VARIETY 'BANI ROSSA' AND A SIMILAR VARIETY

| | 'Bani Rossa' | 'Bante Rossa' (U.S. Plant Pat. No. 18,148) |
|---|---|---|
| Flower count: | More | Fewer |
| Flower size: | Smaller | Larger |
| Branching habit: | More, shorter branches | Fewer, longer branches |
| Plant habit: | More compact | More open |

Plant:

*Form, growth and habit.*—Semi-woody, grown as an annual or perennial; compact and dense mounding habit; well branched.

*Plant height.*—7-10 cm.

*Plant height* (*inflorescence included*).—9-12 cm.

*Plant width.*—21-24 cm.

Foliage:

*Type.*—Opposite.

*Immature, leaf color, upper surface.*—Closest to RHS 137A. Lower surface: Closest to RHS 146A.

*Mature, leaf color, upper surface.*—Darker than RHS 147A. Lower surface: Closest to RHS 146A.

*Length.*—5.0-5.3 cm.

*Width.*—3.3-3.5 cm.

*Shape.*—Ovate.

*Base shape.*—Attenuate.

*Apex shape.*—Acute.

*Margin.*—Serrulate.

*Texture, upper surface.*—Hispid and glandular hairs. Lower surface: Hispid, mostly on veins and glandular hairs.

*Color of veins.*—Both surfaces; RHS 144A basally, otherwise indistinct.

*Petioles color.*—RHS 144A.

*Petioles length.*—1.1-1.4 cm.

*Diameter of petiole.*—0.15-0.2 cm.

*Texture.*—Mostly glandular hairs with a few pilose.

Stem:

*Quantity of main branches per plant.*—About 5.

*Color of stem.*—R.H.S. Lighter than RHS 144A.

*Length of stem.*—9-11 cm.

*Diameter.*—0.2 cm.

*Length of internodes.*—1-2 cm.

*Texture.*—Mostly glandular hairs with a few pilose.

Inflorescence:

*Type.*—Umbel like, flattened semi-sphere the florets are sessile on an ovate receptacle.

*Blooming habit.*—Flowers continuously from spring through fall.

*Number of flowers per inflorescence.*—20-25 open with 6-12 buds.

*Quantity of inflorescences per plant.*—20 -30.

*Lastingness of individual blooms on the plant.*—About 4 weeks (depending on temperatures).

*Fragrance.*—Slightly spicy.

*Umbel horizontal diameter.*—4.0-4.5 cm.

*Umbel vertical height.*—2.0-2.3 cm.

*Color of peduncle.*—RHS 144A.

*Length of peduncle.*—1.5-2.0 cm.

*Peduncle diameter.*—0.15 cm.

*Texture.*—Mostly glandular hairs with a few pilose.

Corolla:

*Form.*—Salver-shaped to shallow cup-shaped, with a relatively long tube at the base. Each floret subtended by a single bract.

*Floret horizontal diameter.*—1-1.3 cm.

*Floret depth.*—1.8-2.0 cm.

*Immature, color of petals, upper surface.*—RHS 9B with slight subdued hues of RHS 187A around the margins.

*Lower surface.*—RHS 12C with blotches of subdued RHS 53C.

*Mature, color of petals, upper surface.*—Closest to RHS 48B with irregular blotches of RHS 54B; maturing to closest to RHS 64B To RHS 64C with about RHS 64A around the corolla opening. Lower surface: RHS 63C with RHS N155B at the margins.

*Petal length.*—0.3-0.4 cm.

*Petal diameter.*—0.3-0.5 cm.

*Apex.*—Mucronulate.

*Margin.*—Entire.

*Shape.*—Obovate.

*Degree of lobation.*—Moderate.

*Texture, upper surface.*—Papillose. Lower surface: Papillose.

*Corolla tube, color, outer surface.*—RHS 64B to RHS 64C. Inner surface: RHS N155B.

*Corolla tube length.*—0.9-1.0 cm.

*Diameter* (*at opening*).—0.2 cm.

*Corolla tube texture, outer surface.*—Glandular hairs. Inner surface: Hirsute and glandular hairs.

Bud (just before opening):

*Color.*—Between RHS 45B and RHS 45C.

*Length.*—0.8-0.9 cm.

*Width.*—0.2-0.3 at the apex.

*Shape.*—Tubular with a flared apex.

Bract:

*Color.*—RHS 144A with a darker apex.

*Length.*—0.4-0.5 cm.

*Diameter.*—0.1-0.15 cm.

*Texture, outer surface.*—Hirsute. Inner surface: Glandular hairs on the inner surface.

Calyx:

*Number of sepals.*—5, fused sepals forming a short tube around the base of each floret.

*Sepal color.*—RHS 144B.

*Length of sepals.*—0.2 cm.

*Width of sepals.*—0.1 cm.

*Sepal shape.*—Tube-shaped with 2 short lobes.

*Apex shape.*—Obtuse.

*Texture, outer surface.*—Hirsute; glandular hairs.

*Inner surface.*—Glabrous.

Reproductive organs:

*Pistil.*—1.

*Pistil length.*—0.5 cm.

*Style color.*—RHS N155D.

*Style length.*—0.4 cm.

*Stigma color.*—RHS 144A.

*Stamens.*—4.

*Color of filaments.*—RHS 155C.

*Length filaments.*—0.6 cm.

*Anther color.*—RHS 54C.

*Length of anthers.*—0.1 cm.

*Anther shape.*—Ovate.

*Pollen amount.*—Sparse.

*Color of pollen.*—RHS 11C.

*Fertility/seed set.*—This hybrid sets very few seeds, and those seeds were not observed for characteristics.

Disease/pest resistance: Disease resistance or susceptibility has not been observed on this hybrid.

What is claimed is:

1. A new and distinct variety of *Lantana* plant named 'Bani Rossa,' substantially as illustrated and described herein.

* * * * *

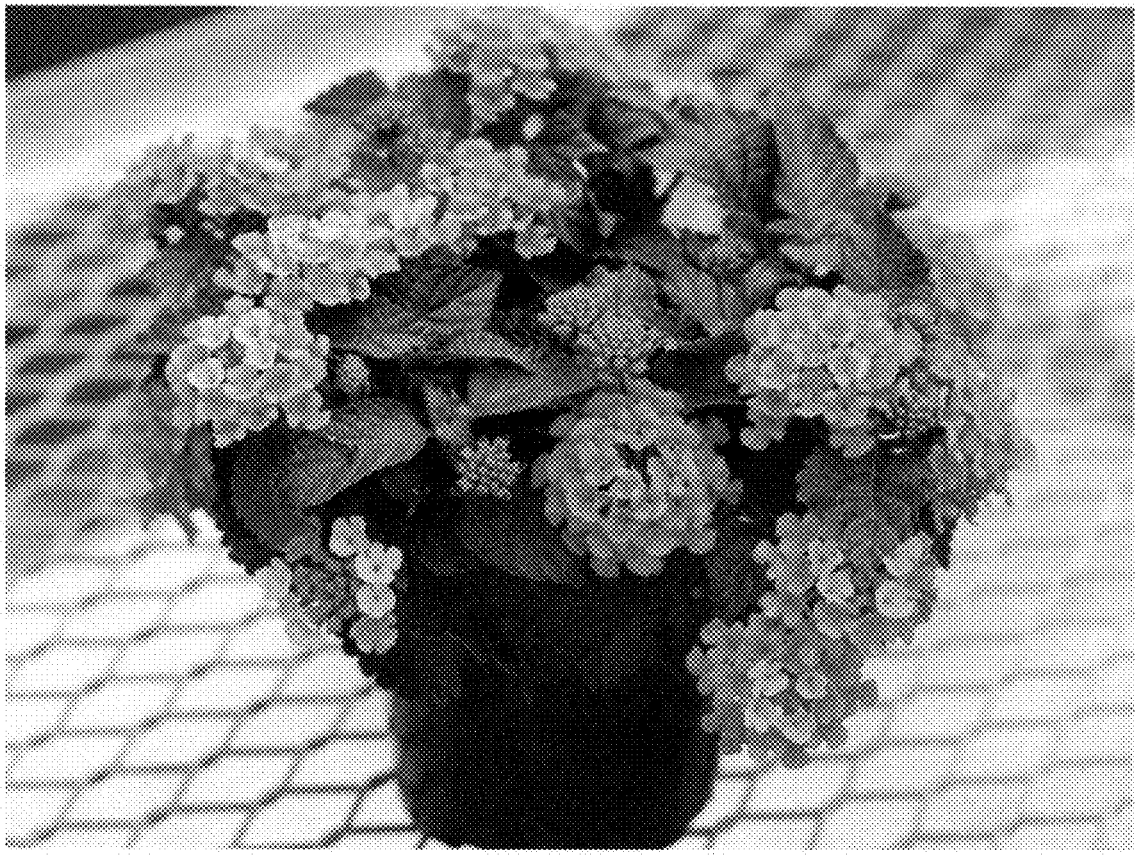
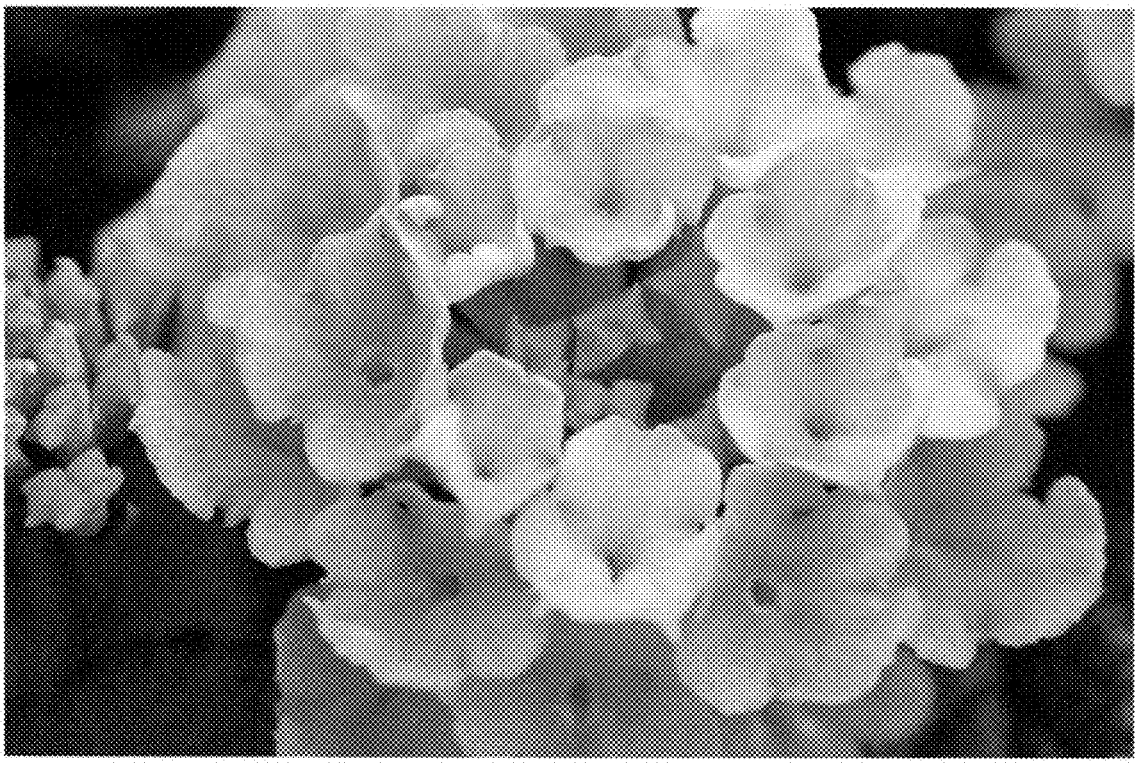

UNITED STATES PATENT AND TRADEMARK OFFICE

CERTIFICATE OF CORRECTION

PATENT NO. : PP21,616 P2
APPLICATION NO. : 12/589238
DATED : January 11, 2011
INVENTOR(S) : Pan It is certified that error appears in the above-identified patent and that said Letters Patent is hereby corrected as shown below:

At column 1, line 36, delete "'Buni Rossa'" and insert therefor --'Bani Rossa'--

Signed and Sealed this
First Day of March, 2011

David J. Kappos

David J. Kappos
*Director of the United States Patent and Trademark Office*